United States Patent [19]

Hewett et al.

[11] Patent Number: 4,875,925

[45] Date of Patent: Oct. 24, 1989

[54] HERBICIDAL METHOD USING DIFLUFENICAN

[75] Inventors: Richard H. Hewett, Thaxted; Brian M. Luscombe, Chelmsford, both of England

[73] Assignee: May & Baker Limited, Dagenham, England

[21] Appl. No.: 74,578

[22] Filed: Jul. 17, 1987

[30] Foreign Application Priority Data

Jul. 21, 1986 [GB] United Kingdom ............... 8617740

[51] Int. Cl.$^4$ ............................................ H01N 43/40
[52] U.S. Cl. ............................................ 71/94; 71/88; 71/90; 71/92; 71/95; 71/98; 71/103; 71/121
[58] Field of Search .................................... 71/94, 121

[56] References Cited

U.S. PATENT DOCUMENTS

| | | | |
|---|---|---|---|
| 3,920,742 | 11/1975 | Lutz et al. ........................ | 71/121 |
| 4,082,537 | 4/1978 | Dudkowski ...................... | 71/121 |
| 4,488,896 | 12/1984 | Lamb et al. ..................... | 71/121 |
| 4,618,366 | 10/1986 | Cramp et al. .................... | 71/94 |

Primary Examiner—Glennon H. Hollrah
Assistant Examiner—Amelia A. Owens
Attorney, Agent, or Firm—Burns, Doane, Swecker & Mathis

[57] ABSTRACT

The present invention relates to a method of controlling the growth of weeds at a locus which comprises applying to the locus (a) a 2,6-dinitroaniline herbicide and (b) diflufenican.

5 Claims, 3 Drawing Sheets

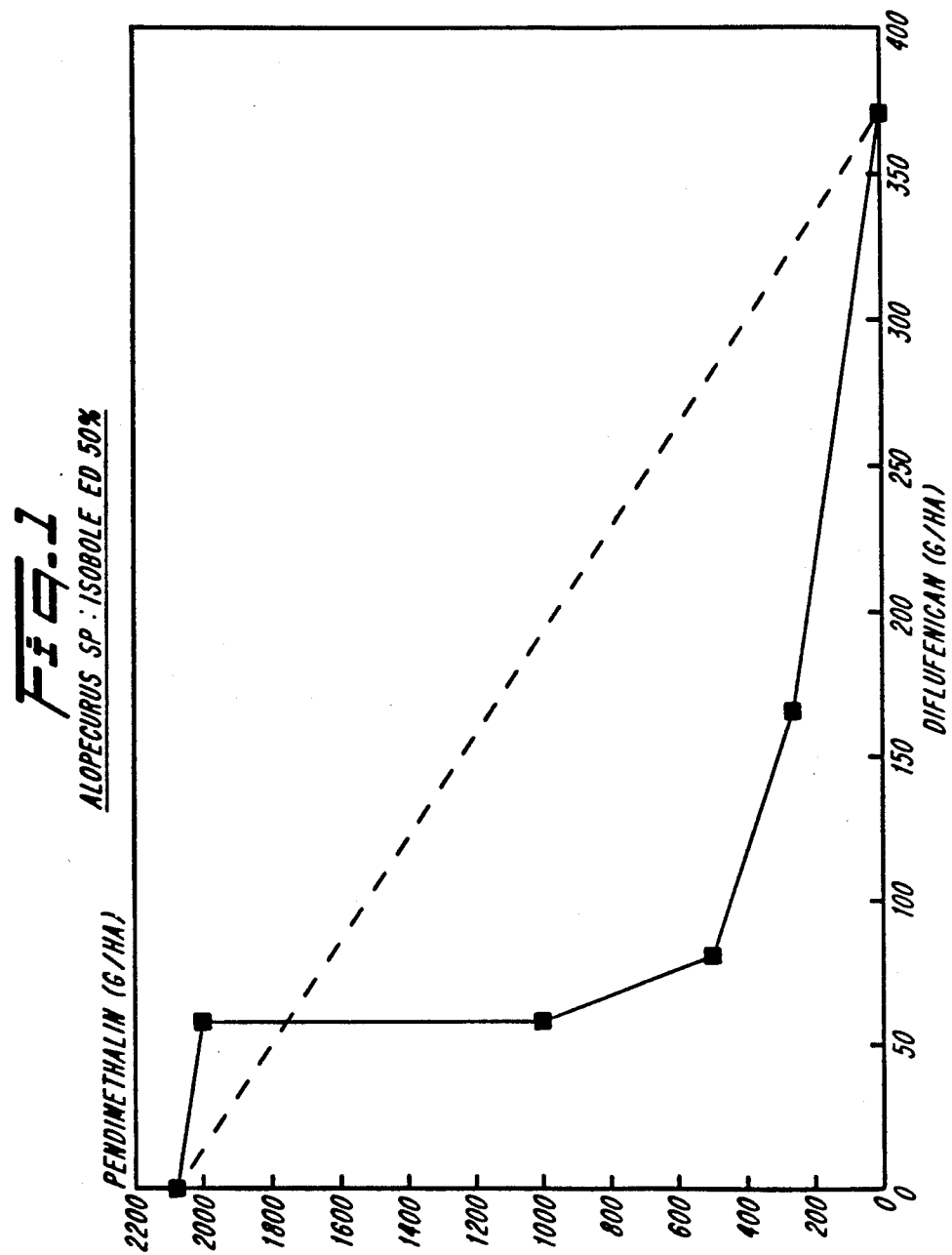

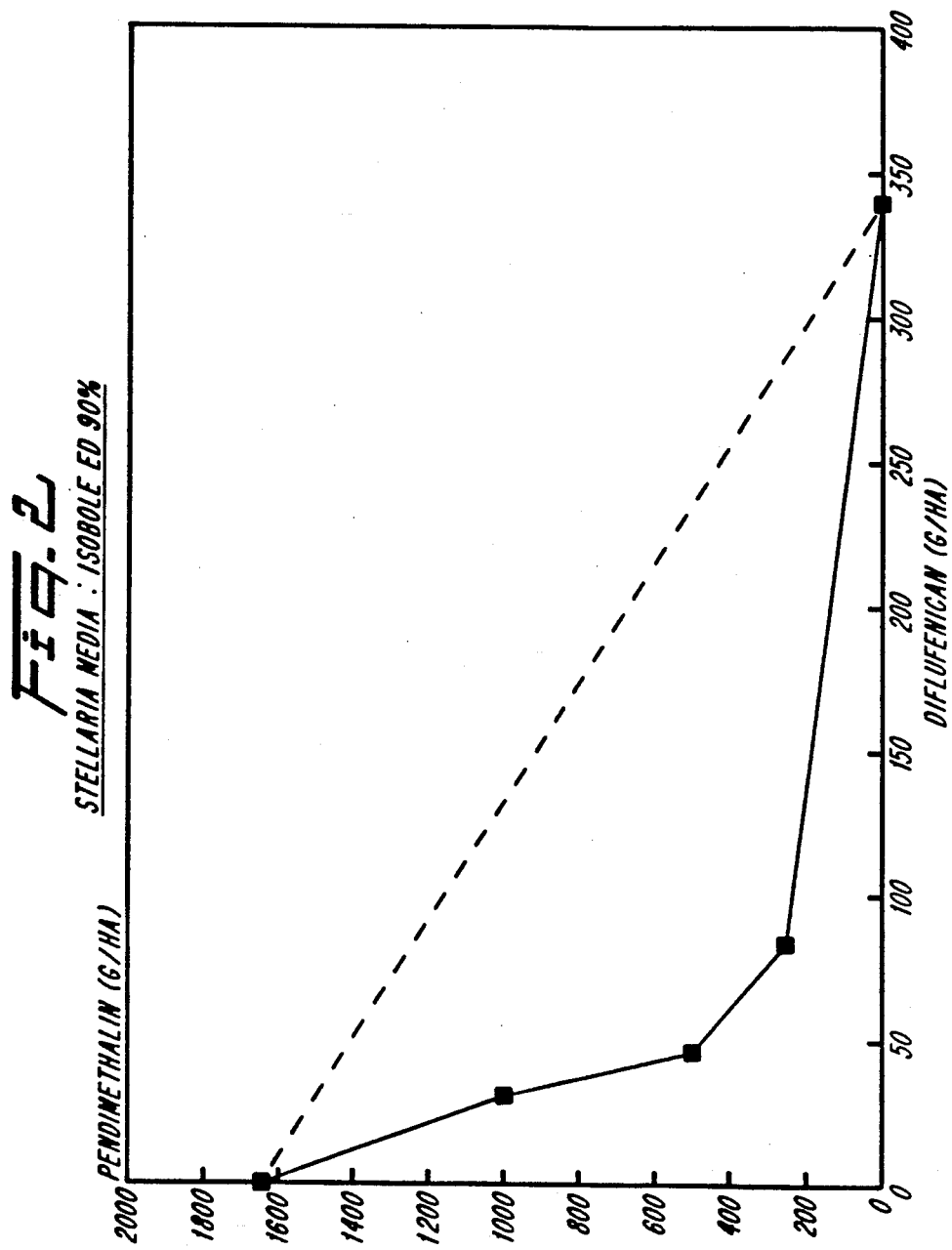

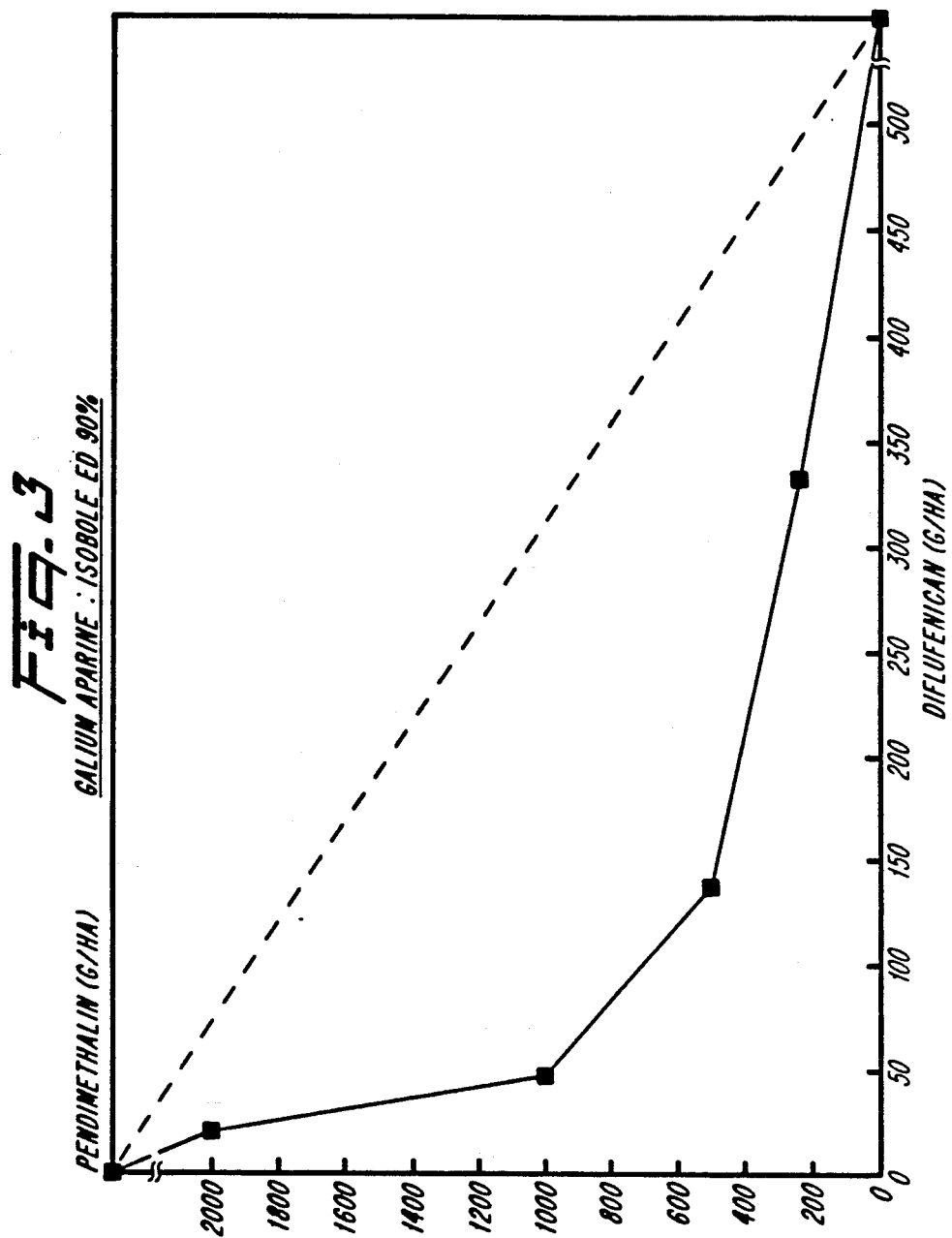

HERBICIDAL METHOD USING DIFLUFENICAN

The present invention relates to new herbicidal compositions comprising N-(2,4-difluorophenyl)-2-(3-trifluoromethylphenoxy)nicotinamide of the formula I depicted hereinafter, which is disclosed in the specification of British Patent No. 2087887B as a pre- and/or post-emergence herbicide, and to their use in agriculture.

2,6-Dinitroaniline herbicides (hereinafter referred to for convenience as the nitroaniline herbicides) are well known in the art and include benfluralin [N-butyl-N-ethyl-2,6-dinitro-4-trifluoromethylaniline], butralin [N-sec-butyl-4-tert-butyl-2,6-dinitroaniline], dinitramine [$N^1,N^1$-diethyl-2,6-dinitro-4-trifluoromethyl-m-phenylenediamine], ethalfluralin [N-ethyl-N-(2-methylallyl)-2,6-dinitro-4-trifluoromethylaniline], fluchloralin [N-(2-chloroethyl)-2,6-dinitro-N-propyl-4-trifluoromethylaniline], isopropalin [4-isopropyl-2,6-dinitro-N,N-dipropylaniline], nitralin [4-methylsulphonyl-2,6-dinitro-N,N-dipropylaniline], pendimethalin [N-(1-ethylpropyl)-3,4-dimethyl-2,6-dinitroaniline], profluralin [N-cyclopropylmethyl-2,6-dinitro-N-propyl-4-trifluoromethylaniline] and trifluralin [2,6-dinitro-N,N-dipropyl-4-trifluoromethylaniline].

Surprisingly, as a result of research and experimentation, it has been discovered that the use of the compound N-(2,4-difluorophenyl)-2-(3-trifluoromethylphenoxy)nicotinamide (hereinafter referred to for convenience as diflufenican) in combination with a nitroaniline herbicide showed an unexpected and remarkable degree of synergism [as defined by P. M. L. Tammes, Netherlands Journal of Plant Pathology, 70 (1964), pp 73–80 in a paper entitled "Isoboles, a graphic representation of synergism in pesticides", or as defined by L. E. Limpel, P. H. Schuldt and D. Lamont, 1962, Proc. NEWCC 16: 48–53, using the following formula (hereinafter referred to as "the Limpel formula"):

$$E = X + Y - \frac{XY}{100}$$

where E = the expected percent inhibition of growth by a mixture of two herbicides at defined doses
X = the percent inhibition of growth by herbicide A at a defined dose
Y = the percent inhibition of growth by herbicide B at a defined dose
When the observed response is greater than expected the combination is synergistic].

The remarkable synergistic effect gives improved reliability of control of a number of weed species and allows for a reduction in the amount of active ingredients employed.

Accordingly the present invention provides a method for controlling the growth of weeds (i.e. undesired vegetation) at a locus which comprises applying to the locus (a) a dinitroaniline herbicide which is preferably a compound of the general formula II wherein $R^1$ represents a straight or branched chain alkyl, alkenyl or alkynyl group containing up to 12 carbon atoms which may be substituted by one or more halogen atoms or straight or branched chain alkoxy groups containing from 1 to 6 carbon atoms, e.g. ethyl, propyl, butyl, 1-ethylpropyl, 2-methylallyl or 2-chloroethyl, a cycloalkyl group containing from 3 to 8 carbon atoms, a cycloalkylalkyl group containing from 3 to 8 carbon atoms in the ring and containing from 1 to 6 carbon atoms in the alkyl moiety, e.g. cyclopropylmethyl, or an arylalkyl (e.g. benzyl) group containing from 7 to 18 carbon atoms which may be ring-substituted by one or more halogen atoms or straight or branched chain alkyl or alkoxy groups containing from 1 to 6 carbon atoms, $R^2$ represents the hydrogen atom or a group $R^1$ as hereinbefore defined, $R^1$ and $R^2$ being the same or different, or $R^1$ and $R^2$ together with the nitrogen atom to which they are attached represent a saturated heterocyclic group containing from 4 to 7 ring members optionally containing a further hetero atom O, S or N (which nitrogen may be alkylated), e.g. pyrrolidinyl or piperidino, $R^4$ represents a hydrogen or halogen atom, a straight or branched chain alkyl group containing from 1 to 12 carbon atoms which may be substituted by one or more halogen atoms or straight or branched chain alkoxy groups containing from 1 to 6 carbon atoms, a cycloalkyl group containing from 3 to 8 carbon atoms, a straight or branched chain alkylthio, alkylsulphinyl or alkylsulphonyl group containing from 1 to 6 carbon atoms or the sulphamoyl group which may be substituted by one or two substituents represented by the symbol $R^1$ and $R^3$ represents a group $R^4$ as hereinbefore defined, $R^3$ and $R^4$ being the same or different, (preferably $R^3$ represents the hydrogen atom or an alkyl group) or the substituted amino group —$NR^1R^2$ or the unsubstituted amino group and (b) diflufenican, which is N-(2,4-difluorophenyl)-2-(3-trifluoromethylphenoxy)nicotinamide. For this purpose, the nitroaniline herbicide and diflufenican are normally used in the form of herbicidal compositions (i.e. in association with compatible diluents or carriers and/or surface-active agents suitable for use in herbicidal compositions), for example as hereinafter described.

Preferred compounds of general formula II are those wherein $R^1$ represents a straight or branched chain alkyl group containing from 1 to 12 carbon atoms which may be substituted by one or more halogen atoms or straight or branched chain alkoxy groups containing from 1 to 6 carbon atoms, a straight or branched chain alkenylmethyl group containing up to 12 carbon atoms, a cycloalkyl group containing from 3 to 8 carbon atoms, a cycloalkylalkyl group containing from 3 to 8 carbon atoms in the ring and containing from 1 to 6 carbon atoms in the alkyl moiety or a benzyl group which may be ring-substituted by one or more halogen atoms or straight or branched chain alkyl or alkoxy groups containing from 1 to 6 carbon atoms, e.g. 2-chloro-6-fluorobenzyl, and $R^2$ represents the hydrogen atom or a straight or branched chain alkyl group containing from 1 to 6 carbon atoms, e.g. ethyl or propyl.

Compounds of general formula II wherein $R^3$ represents a hydrogen or halogen atom or a straight or branched chain alkyl group containing from 1 to 12 carbon atoms which may be substituted by one or more halogen atoms, e.g. methyl, or the unsubstituted amino group and $R^4$ represents a halogen atom, a straight or branched chain alkyl group containing from 1 to 12 carbon atoms which may be substituted by one or more halogen atoms, e.g. isopropyl, t.butyl or trifluoromethyl, a straight or branched chain alkylsulphonyl group containing from 1 to 6 carbon atoms, e.g. methanesulphonyl, or the sulphamoyl group are also preferred.

Especially preferred compounds of general formula II are
N-sec-butyl-4-tert-butyl-2,6-dinitroaniline, N-butyl-N-ethyl-2,6-dinitro-4-trifluoromethylaniline,
N-ethyl-N-(2-methylallyl)-2,6-dinitro-4-trifluoromethylaniline,
N-(2-chloro-6-fluorobenzyl)-N-ethyl-2,6-dinitro-4-trifluoromethylaniline,
N-(2-chloroethyl)-2,6-dinitro-N-propyl-4-trifluoromethylaniline,
N-cyclopropylmethyl-2,6-dinitro-N-propyl-4-trifluoromethylaniline,
N-(2-methylallyl)-2,6-dinitro-N-propyl-4-trifluoromethylaniline,
$N^1,N^1$-diethyl-2,6-dinitro-4-trifluoromethyl-m-phenylenediamine,
2,6-dinitro-$N^1,N^1$-dipropyl-4-trifluoromethyl-m-phenylenediamine,
4-isopropyl-2,6-dinitro-N,N-dipropylaniline,
4-methylsulphonyl-2,6-dinitro-N,N-dipropylaniline,
3,5-dinitro-$N^4,N^4$-dipropylsulphanilamide,
2,6-dinitro-N,N-dipropyl-4-trifluoromethylaniline and
N-(1-ethylpropyl)-3,4-dimethyl-2,6-dinitroaniline, the last two of which are known respectively as trifluralin and pendimethalin.

Trifluralin and pendimethalin are more especially preferred.

The amounts of the nitroaniline herbicide and diflufenican applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates from 250 g to 2000 g of the nitroaniline herbicide and from 50 g to 250 g of the diflufenican per hectare give good results. However, it is to be understood that higher or lower applications rates may be used, depending upon the particular problem of weed control encountered.

The nitroaniline herbicide and diflufenican in combination may be used to control selectively the growth of weeds, for example to control the growth of those species hereinafter mentioned, by pre- or post-emergence application in a directional or non-directional fashion, e.g. by directional or non-directional spraying, to a locus of weed infestation which is an area used, or to be used, for growing crops, for example cereals, e.g. wheat, barley or pre-emergence to, for example, maize, legumes, e.g. soya beans, oilseed crops, e.g. sunflower or oilseed rape, before or after sowing of the crop or before or after emergence of the crop. For the selective control of weeds at a locus of weed infestation which is an area used, or to be used, for the growing of crops, e.g. the crops hereinbefore mentioned, application rates from 250 g to 2000 g of the nitroaniline herbicide and from 50 g to 250 g of diflufenican per hectare are particularly suitable.

According to a feature of the present invention, there is provided a method for the control of the growth of weeds by pre- or post-emergence application which comprises the combined use of (a) a nitroaniline herbicide, especially trifluralin or pendimethalin, and (b) diflufenican, for example at application rates of from 500 to 2000 (preferably from 500 to 1000) g/ha, and from 50 to 250 (preferably from 50 to 125) g/ha respectively, of (a) and (b) in proportions of 40:1 to 2:1 (preferably 20:1 to 4:1) by weight of (a) to (b), to control a very wide spectrum of annual broad-leafed weeds and grass weeds in crops, e.g. the crops hereinbefore mentioned, for example cereals, e.g. wheat and barley, without significant permanent damage to the crop. The combined use described above offers both foliar and residual activity and consequently can be employed over a long period of crop development, i.e. from pre-weed pre-crop emergence to post-weed post-crop emergence.

By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

Weeds that may be controlled by the method include:—from broad-leaf weeds, *Amaranthus retroflexus, Amsinckia intermedia, Anagallis arvensis, Anthemis arvensis, Anthemis cotula, Atriplex patula, Brassica nigra, Capsella bursa-pastoris, Chenopodium album, Cirsium arvense, Galium aparine, Ipomea purpurea, Lamium amplexicaule, Lamium purpureum, Lapsana communis, Matricaria inodora, Montia linearis, Montia perfoliata, Papaver rhoeas,* Polygonum spp. (e.g. *Polygonum aviculare*), *Portulaca oleracea, Raphanus raphanistrum, Senecio vulgaris, Sinapis arvensis, Solanum nigrum, Sonchus arvensis, Spergula arvensis, Stellaria media, Thlaspi arvense, Urtica urens, Veronica hederifolia, Veronica persica, Vicia sativa, Viola arvensis,* and from grass weeds *Alopecurus myosuroides, Apera spica-venti, Argrostis stolonifera, Poa annua, Poa trivialis, Digitaria sanguinalis, Echinochloa crus-galli, Eleusine indica, Setaria viridis,* Brachiaria spp. (e.g. *Brachiaria plantaginea*) and *Sorghum halepense.*

The pattern of persistence of the nitroaniline herbicide and the diflufenican allow the method of the present invention to be practised by the time-separated application of separate formulations.

In accordance with usual practice, a tank mix may be prepared prior to use by combining separate formulations of the individual herbicidal components.

The following Experiments illustrate the present invention:

EXPERIMENT 1

The following greenhouse experiment demonstrates the synergistic activity of the combined use of pendimethalin and diflufenican in controlling the growth of certain weeds by pre-emergence application. Greenhouse experiment showing the nature of biological synergism between pendimethalin and diflufenican applied pre-emergence A factorial experiment with 30 treatments was carried out to investigate the interaction of pendimethalin and diflufenican at a wide range of doses i.e. 0, 250, 500, 1000 and 2000 g/ha of pendimethalin plus diflufenican at 0, 31, 62, 125, 250 and 500 g/ha.

All treatments were made in an appropriate volume of water by using appropriate quantities of a 33% w/v emulsifiable concentrate of pendimethalin (commercial product) and diflufenican formulated as an experimental aqueous suspension concentrate (Example 2 hereinafter) containing 50% w/v active ingredient to give the above dose rates in a spray volume of 290 l/ha. All treatments were applied using a laboratory sprayer fitted with a Sparying Systems Teejet SS 8003E operating at 2.94 kgf/cm$^2$. Treatments were applied to about 20 *Alopecurus myosuroides* seeds sown 1 cm deep in a loamy soil in 7.5 cm square pots. There were 4 replicate pots per treatment which were arranged in a randomised block design in a glasshouse after treatment. The pots were watered by a combination of overhead irrigation and sub-irrigation. A visual assessment of weed control was made 22 days after treatment as a percentage compared to the untreated pots. The mean percentage weed control was calculated and from these results the 50% herbicidally effective dose (ED$_{50}$) in grams of diflufenican per hectare was calculated for diflufenican alone and in mixtures with pendimethalin. The following values were obtained:

|  | ED$_{50}$ |
| --- | --- |
| diflufenican alone | 370 |
| diflufenican with 250 g pendimethalin/ha | 166 |
| diflufenican with 500 g pendimethalin/ha | 80 |
| diflufenican with 1000 g pendimethalin/ha | 58 |
| diflufenican with 2000 g pendimethalin/ha | 59 |

The ED$_{50}$ of pendimethalin alone was found to be 2071 g/ha.

The values above were then used to plot an ED$_{50}$ isobole for a two-sided effect (Tammes, op. cit. p. 75) where both compounds were active. The isobole produced, shown hereinafter in FIG. I, was clearly a type III isobole (Tammes, op. cit. p. 75) which is characteristic of synergism.

EXPERIMENT 2

Greenhouse experiment showing the nature of biological synergism between pendimethalin and diflufenican applied post-emergence A similar experiment to that hereinbefore described in Experiment 1 was carried out with pendimethalin and diflufenican applied to either 4 plants of *Stellaria media* at the 2 leaf stage or 4 plants of *Galium aparine* at the 2 whorl (branching initiated) stage. The following 90% herbicidally effective doses (ED90) in grams of diflufenican per hectare were calculated from the mean percentage weed control 14 days after treatment.

| *Stellaria media* | ED$_{90}$ |
| --- | --- |
| diflufenican alone | 340 |
| diflufenican with 250 g pendimethalin/ha | 82 |
| diflufenican with 500 g pendimethalin/ha | 45 |
| diflufenican with 1000 g pendimethalin/ha | <31 |

The ED$_{90}$ of pendimethalin alone was found to be 1653 g/ha.

| *Galium aparine* | ED$_{90}$ |
| --- | --- |
| diflufenican alone | >500 |
| diflufenican with 250 g pendimethalin/ha | 326 |
| diflufenican with 500 g pendimethalin/ha | 139 |
| diflufenican with 1000 g pendimethalin/ha | 47 |
| diflufenican with 2000 g pendimethalin/ha | 19 |

The ED$_{90}$ of pendimethalin alone was found to be greater than 2000 g/ha.

The symbols "<" and ">" mean "less than" and "greater than" respectively.

The values above were used to plot ED$_{90}$ isoboles for a two-sided effect (Tammes, op. cit. p. 75) where both compounds were active. The isoboles produced for *Stellaria media* and *Galium aparine* (shown hereinafter in FIGS. II and III respectively), were clearly type III isoboles (Tammes, op. cit. p. 75) which are characteristic of synergism.

EXPERIMENT 3

Diflufenican formulated as a 50% w/v aqueous suspension concentrate (Example 2), trifluralin as a 48% w/v emulsifiable concentrate (commercial product and a mixed formulation of diflufenican and trifluralin containing 44% w/v total active ingredient (Example 6) were applied at 0.16 l, 1.67 l and 2 l/ha respectively pre-emergence and just at emergence to winter barley and winter wheat to control *Lamium purpureum* pre-emergence under field conditions. The treatments were applied to three replicate 30 m$^2$ plots in a spray volume of 220 l/ha (winter barley) and 206 l/ha (winter wheat) using a motorised small plot sprayer. Visual % phytotoxicity was recorded and the results are given below.

| Winter barley (variety Igri) | Maximum % crop phytotoxicity | % weed phytotoxicity 72 days after spraying |
| --- | --- | --- |
| Diflufenican 80 g/ha (A) | 5.8 | 40 |
| Trifluralin 800 g/ha (B) | 0 | 20 |
| Diflufenican 80 + Trifluralin 800 g/ha (A + B) | 2.5 | 76 (Expected by application of Limpel formula:52%) |

| Winter wheat (variety Galahad) | Maximum % crop phytotoxicity | % weed phytotoxicity 98 days after spraying |
| --- | --- | --- |
| Diflufenican 80 g/ha (A) | 0 | 80 |
| Trifluralin 800 g/ha (B) | 0 | 5 |
| Diflufenican 80 + Trifluralin 800 g/ha (A + B) | 2.5 | 100 (Expected by application of Limpel formula:81%) |

These results show clearly that the combination was synergistic against *Lamium purpureum* as the observed weed control for the combination of the two herbicides was much greater than expected.

According to a feature of the invention, there is provided a product comprising (a) a nitroaniline herbicide and (b) diflufenican as a combined preparation for simultaneous, separate or sequential use in controlling the growth of weeds at a locus.

According to a further feature of the present invention, there is provided compositions suitable for herbicidal use comprising (a) a nitroaniline herbicide and (b) diflufenican, for example in porportions of 40:1 to 1:1 w/w of (a) to (b) [preferably 40:1 to 2:1 and more preferably 20:1 to 4:1 w/w of (a) to (b)] in association with, and preferably homogeneously dispersed in, one or more compatible herbicidally-acceptable diluents or carriers and/or surface-active agents (i.e. diluents or carriers or surface-active agents of the type generally accepted in the art as being suitable for use in herbicidal compositions and which are compatible with the nitroaniline herbicide and diflufenican). The term "homogeneously dispersed" is used to include compositions in which the nitroaniline herbicide and diflufenican are dissolved in the other components. The term "herbicidal compositions" is used in a broad sense to include not only compositions which are ready for use as herbicides but also concentrates which must be diluted before use. Preferably, the compositions contain from 0.05 to 90% by weight of the triazine herbicide and diflufenican.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the nitroaniline herbicide and diflufenican with solid diluents or by impregnating the solid diluents or carriers with solutions of the nitroaniline herbicide and diflufenican in volatile solvents, evaporating the solvents and, if necessary, grinding the products so as to obtain powders. Granular formulations may be prepared by absorbing the nitroaniline herbicide and diflufenican (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral and vegetable oils, particularly in the case of liquid concentrates in which the diluent or carrier is an oil, to give compositions ready for use. When desired, liquid compositions of the nitroaniline herbicide and diflufenican may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of the nitroaniline herbicide and diflufenican, from 2 to 10% w/v of surface-active agent, from 0.1 to 5% w/v of thickener and from 15 to 87.9% by volume of water; wettable powders which comprise from 10 to 90% w/w of the nitroaniline herbicide and diflufenican, from 2 to 10% w/w of surface-active agent and from 8 to 88% w/w of solid diluent or carrier; liquid water soluble concentrates which comprise from 10 to 30% w/v of the nitroaniline herbicide and diflufenican, from 5 to 25% w/v of surface-active agent and from 45 to 85% by volume of water-miscible solvent, e.g. dimethylformamide; liquid emulsifiable suspension concentrates which comprise 10 to 70% w/v of the nitroaniline herbicide and diflufenican, from 5 to 15% w/v of surface-active agent, from 0.1 to 5% w/v of thickener and from 10 to 84.9% by volume of organic solvent; granules which comprise from 2 to 10% w/w of the nitroaniline herbicide and diflufenican, from 0.5 to 2% w/w of surface-active agent and from 88 to 97.5% w/w of granular carrier and emulsifiable concentrates which comprise from 0.05 to 90% w/v, and preferably from 1 to 60% w/v, of the nitroaniline herbicide and diflufenican, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the nitroaniline herbicide and diflufenican in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [α-chloro-2,6-diethyl-N-(methoxymethyl)acetanilide], benzoylprop-ethyl [ethyl N-benzoyl-N-(3,4-dichlorophenyl-2-aminopropionate], bromoxynil [3,5-dibromo-4-hydroxybenzonitrile], carbetamide [D-N-ethyl-2-(phenylcarbamoyloxy)propionamide], chlorfenpropmethyl [methyl 2-chloro-2-(4-chlorophenyl)-propionate], chlortoluron [N'-(3-chloro-4-methyphenyl)-N,N-dimethylurea], 2,4-D [2,4-dichlorophenoxyacetic acid], 2,4-DB [4-(2,4-dichlorophenoxy)-butyric acid], diallate [S-2,3-dichloroallyl-N,N-di-isopropyl(thiocarbamate)], dicamba [3,6-dichloro-2- methoxybenzoic acid], dichlorprop [(±)-2-(2,4-dichlorophenoxy)propionic acid], diclofop [(RS)-2-[4-(2,4-dichlorphenoxy)phenoxy]propionic acid], difenzoquat [1,2-dimethyl-3,5-diphenylpyrazolium salts], dimefuron [4-[2-chloro-4-(3,3-dimethylureido)phenyl]-2-t-butyl-1,3,4-oxadiazolin-5-one], diuron [N'-(3,4-dichlorophenyl)-N,N-dimethylurea], flampropisopropyl [isopropyl (±)-2-(N-benzoyl-3-chloro-4-fluoroanilino)propionate], flamprop-methyl [methyl (±)-2-(N-benzoyl-3-chloro-4-fluoroanilino)propionate], ioxynil [4-hydroxy-3,5-diiodobenzonitrile], isoproturon [N'-(4-isopropylphenyl)-N,N-dimethylurea], linuron [N'-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop [(±)-2-(4-chloro-2-methyl-phenoxy)-propionic acid], methabenzthiazuron [N-(benzothiazol-2-yl)-N,N'-dimethylurea], metribuzin [4-amino-6-t-butyl-3-(methylthio)-1,2,4-triazin-5(4H)-one], paraquat [1,1'-dimethyl-4,4'-bipuridylium salts], tri-allate [S-2,3,3-trichloroallyl N,N-di-isopropylthiocarbamate], atrazine [2-chloro-4-ethylamino-6-isopropylamino-1,3,5-triazine], and simazine [2-chloro-4,6-bis(ethylamino)-1,3,5-triazine]; insecticides, e.g. carbaryl [naphth-1-yl N-methylcarbamate] and synthetic pyrethroids, e.g. permethrin and cypermethrin; and fungicides, e.g. 2,6-dimethyl-4-tridecylmorpholine, methyl N-(1-butylcarbamoylbenzimidazol-2-yl)carbamate, 1,2-bis-(3-methoxycarbonyl-2-thioureido)benzene, isopropyl 1-carbamoyl-3-(3,5-dichlorophenyl)hydantoin and 1-(4-chloro-phenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethanephosphonic acid; and fertilizers containing, for example, nitrogen, potassium and phosphorus and trace elements known to be essential to successful plant life, e.g. iron, magnesium, zinc, manganese, cobalt and copper.

Pesticidally active compounds and other biologically active materials which may included in, or used in conjunction with, the herbicidal compositions of the present invention, for example those hereinbefore mentioned, and which are acids, may, if desired, be utilized in the form of conventional derivatives, for example alkali metal and amine salts and esters.

The compositions of the invention may be made up as an article of manufacture comprising a nitroaniline herbicide and diflufenican and optionally other biologically active compounds as hereinbefore described or, as is preferred, a herbicidal composition as hereinbefore described, and preferably a herbicidal concentrate which must be diluted before use, comprising the nitroaniline herbicide and diflufenican within a container for the aforesaid nitroaniline herbicide and diflufenican or a said herbicidal composition, and instructions physically associated with the aforesaid container setting out the manner in which the aforesaid nitroaniline herbicide and diflufenican or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least 0.5 hectares of ground to control the growth of seeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application from 250 g to 2000 g of the nitroaniline herbicide and from 50 g to 250 g of diflufenican per hectare in the manner and for the purposes hereinbefore described.

The following Examples illustrate herbicidal compositions according to the present invention.

EXAMPLE 1

A wettable powder was formed from the following ingredients in the usual manner:

| | |
|---|---|
| diflufenican | 50% w/w |
| Nekal BX (sodium alkyl naphthalene sulphonate) | 10% w/w |
| sodium lignosulphonate | 3% w/w |
| Sopropon T36 (sodium polycarboxylate) | 0.5% w/w |
| Hymod AT (ball clay) | to 100% w/w |

EXAMPLE 2

An aqueous suspension concentrate was formed from the following ingredients in the usual manner:

| | |
|---|---|
| diflufenican | 50% w/v |
| Ethylan BCP (a nonylphenol-ethylene oxide condensate containing 9 moles of ethylene oxide per mole of phenol) | 0.5% w/v |
| Soprophor FL (triethanolamine salt of oxyethylated polyarylphenolphosphate) | 1.0% w/v |
| Sopropon T36 (sodium polycarboxylate) | 0.5% w/v |
| Antifoam FD | 0.1% w/v |
| Rhodigel 23 (xanthan gum) | 0.2% w/v |
| dichlorophen sodium solution, 40% w/w | 0.25% w/v |
| water | to 100% |

EXAMPLE 3

| A wettable powder was formed from:- | |
|---|---|
| pendimethalin | 40% w/w |
| diflufenican | 2% w/w |
| Arylan S (sodium dodecyl benzene sulphonate) | 2% w/w |
| Darvan No. 2 (sodium lignosulphonate) | 5% w/w |
| Aerosil (silicon dioxide of microfine particle size) | 5% w/w |
| Celite PF (synthetic magnesium silicate carrier) | 46% w/w | by mixing the ingredients and grinding the mixture in a hammer mill to give a wettable powder which may be diluted with water and applied at a rate of 4 kg per hectare in 200 liters of spray fluid per hectare to control a wide range of grass and broad-leaf weeds by pre- or post-emergence application to a crop of barley.

EXAMPLE 4

An aqueous suspension concentrate was formed from:

| | |
|---|---|
| pendimethalin | 40% w/v |
| diflufenican | 10% w/v |
| Ethylan BCP (a nonylphenol-ethylen oxide condensate containing 9 moles of ethylene oxide per mole of phenol] | 2% w/v |
| Antifoam FD (silicone emulsion antifoaming agent) | 0.5% w/v |
| Pluronic L62 (an ethylene oxide/ propylene oxide block co-polymer) | 2% w/v |
| Sopropon T36 (sodium salt of polycarboxylic acid) | 0.5% w/v |
| Attagel 50 (swelling attapulgite clay) | 0.5% w/v |
| water | to 100% | by intimately mixing the ingredients and grinding in a ball-mill for 24 hours. The concentrate thus obtained may be dispersed in water and applied at an application rate of 45 liters per hectare pre-emergence to a crop of wheat to control a wide range of broad leaf weeds.

EXAMPLE 5

A water dispersible granule form was formed by granulating the ingredients used in Example 3 with water using a pan granulator into granules of 0.1–2 mm diameter. These granules can then be dispersed at a rate of 3 kg in 200 liters of water per hectare to control a wide range of broad-leaf weeds by pre- or post-emergence application to a crop of barley.

EXAMPLE 6

An emulsifiable suspension concentrate was prepared from:

| | |
|---|---|
| trifluralin | 40% w/v |
| diflufenican | 4% w/v |
| Tensiofix B7438 (mixture of anionic, nonionic surface active agents) | 7.5% w/v |
| Soprophor BSU (polyaryl phenol ethoxylate) | 2.6% w/v |
| Aerosil R974 (fumed hydrophobic silica) | 2.5% w/v |
| Olin 10G (50% nonylphenol glycidol surfactant in water) | 0.053% w/v |
| Antifoam FD (silicone based antifoam emulsion) | 0.005% w/v |
| water | about 2.5% w/v |
| light aromatic $C_{10}$ solvent | to 100% |

The diflufenican was blended in an aqueous solution of some Soprophor BSU, Olin 10G, Antifoam FD and water. This was milled through a bead mill to an average particle size of 0.003 mm, and then blended with a solution of the remaining ingredients in aromatic $C_{10}$ solvent under high shear. The resulting formulation was then applied at 2 l in 200 l of water pre-emergence to one hectare of wheat to control *Lamium purpureum*, *Montia perfoliata*, *Poa annua*, *Raphanus raphinistrun*, *Stellaria media*, *Tripleurospermum maritimum* (*Matricaria inodora*), *Veronica persica* and *Viola arvensis*.

In the mixed formulations in the Examples described hereinbefore, the nitroaniline herbicide may be replaced by the appropriate quantities of other nitroaniline herbicides.

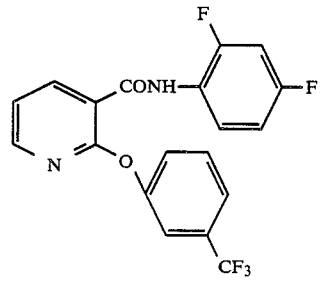

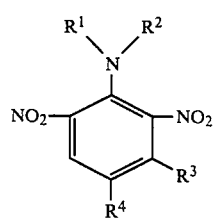

We claim:

1. A method of controlling the growth of *Galium aparine* at a locus which comprises applying to the locus an effective amount of (a) pendimethalin and (b) diflufenican, which is N-(2,4-difluorophenyl)-2-(3-trifluoromethylphenoxy)nicotinamide, wherein the ratio of (a) to (b) is from 20:1 to 4:1 by weight.

2. A method according to claim 1 in which the pendimethalin and diflufenican are applied at application rates of from 500 to 1000 g/ha and from 50 to 125 g/ha, respectively.

3. A product comprising an effective amount of (a) pendimethalin and (b) diflufenican, which is N-(2,4-difluorophenyl)-2-(3-trifluoromethylphenoxy)-nicotinamide, wherein the ratio of (a) to (b) is from 20:1 to 4:1 by weight, as a combined preparation for simultaneous, separate or sequential use in controlling the growth of weeds at a locus.

4. A herbicidal composition which comprises an effective amount of (a) pendimethalin and (b) diflufenican, which is N-(2,4-difluorophenyl)-2-(3-trifluoromethylphenoxy)-nicotinamide, wherein the ratio of (a) to (b) is from 20:1 to 4:1 by weight, in association with a herbicidally acceptable diluent or carrier and/or surface active agent.

5. A herbicidal composition according to claim 4, which comprises from 0.05 to 90% by weight of diflufenican and pendimethalin.

* * * * *

UNITED STATES PATENT AND TRADEMARK OFFICE
CERTIFICATE OF CORRECTION

PATENT NO.  : 4,875,925
DATED       : October 24, 1989
INVENTOR(S) : Richard H. HEWETT et al It is certified that error appears in the above-identified patent and that said Letters Patent is hereby corrected as shown below:

Column 5, line 6, delete "Sparying" and insert -- Spraying --;

Column 9, line 7, delete "flampropisopro" and insert -- flamprop-isopro --;

Column 9, line 20, delete "bipuridylium" and insert -- bipyridylium --; and

Column 11, line 8, delete "ethylen" and insert -- ethylene--.

Signed and Sealed this

Third Day of March, 1992

Attest:

HARRY F. MANBECK, JR.

*Attesting Officer*　　　　Commissioner of Patents and Trademarks